United States Patent [19]

Wirth et al.

[11] Patent Number: 5,380,856
[45] Date of Patent: Jan. 10, 1995

[54] PROCESS FOR PREPARATION OF A POLYMORPHIC FORM OF TERPHENADINE HAVING A HIGH MELTING POINT AND ENHANCED PURITY, AND THE PRODUCT THUS OBTAINED

[75] Inventors: Didier G. Wirth; Marcel Deglave, both of Paris; Marc-Henri Mouton, Sannois, all of France

[73] Assignee: Isochem, Paris, France

[21] Appl. No.: 117,208

[22] PCT Filed: Oct. 1, 1992

[86] PCT No.: PCT/FR92/00949

§ 371 Date: Sep. 13, 1993

§ 102(e) Date: Sep. 13, 1993

[87] PCT Pub. No.: WO93/07121

PCT Pub. Date: Apr. 15, 1993

[30] Foreign Application Priority Data

Oct. 1, 1991 [FR] France .................... 91 18064

[51] Int. Cl.⁶ .......................................... C07D 211/20
[52] U.S. Cl. ................................................... 546/248
[58] Field of Search ........................................ 546/248

[56] References Cited

FOREIGN PATENT DOCUMENTS 0339118  2/1989  European Pat. Off. ............ 546/248
0346765 12/1989  European Pat. Off. ............ 546/248
0385375  9/1990  European Pat. Off. ............ 546/248
0396100 11/1990  European Pat. Off. ............ 546/248

OTHER PUBLICATIONS

Badwan, Analytical Profiles of Drug Substances, vol. 19 (1990), pp. 628–662.

*Primary Examiner*—C. Warren Ivy
*Assistant Examiner*—Raymond Covington
*Attorney, Agent, or Firm*—Sughrue, Mion, Zinn, Macpeak & Seas

[57] ABSTRACT

The invention concerns a process for preparation of a polymorphic form of terphenadine having a high melting point and enhanced purity, according to which water and a raw terphenadine solution are mixed in dimethylformamide and the pure terphenadine thus precipitated is collected.

The invention also concerns the product obtained.

7 Claims, No Drawings

PROCESS FOR PREPARATION OF A POLYMORPHIC FORM OF TERPHENADINE HAVING A HIGH MELTING POINT AND ENHANCED PURITY, AND THE PRODUCT THUS OBTAINED

The present invention concerns a process for preparation of the polymorphic form of terphenadine having a high melting point and enhanced purity, this process consisting of crystallization using a mixture of water and dimethylformamide H—CO—N(CH3)2.

Terphenadine, or α[4-(1,1-dimethylethyl)phenyl]-4-(hydroxy-diphenylmethyl)-1-piperidine butanol, is a non-sedative, antihistaminic substance belonging to the group of histamine 1 antagonists.

One conventional terphenadine-synthesis process is as follows:

A mixture of:
α, α-diphenyl-4-piperidine methanol (I), 1-4-(1,1-dimethyl ethyl) phenyl-4-chloro-1-butanone (II), potassium bicarbonate, and potassium iodide in toluene is treated under reflux and while being stirred at ambient temperature.

The lukewarm reactive mixture is filtered, and the cooled filtrate is treated with an excess amount of ethereal chlorhydric acid.

The precipitate thus obtained is crystallized twice using a methanol/isopropanol mixture in order to obtain the 1-4-(1,1-dimethyl ethyl)phenyl-4-4-(hydroxidiphenyl methyl)-1-piperidinyl-1-butanone hydrochloride (III).

A solution of (III) is treated in methanol using a solution of potassium hydroxide in methanol, until it becomes basic.

The resulting mixture is cooled, stirred, and treated in parts with potassium borohydride. The cooling bath is removed and the reaction product is stirred and then concentrated on a vapor bath under reduced pressure, so as to obtain a solid residue.

After washing in water and two recrystallization operations utilizing acetone, terphenadine (IV) is obtained.

It appears that terphenadine can take on several polymorphic forms.

Until now, three distinct polymorphic forms and two solvation products have been identified.

These forms were produced from recrystallization of terphenadine in different solvents.

Polymorphic Form I: obtained by recrystallization of a methanol/water mixture ($t_f$ of between 149° C. and 152° C.).

Polymorphic Form II: obtained by recrystallization of methanol ($t_f$ of between 146° C. and 148° C.).

Polymorphic Form III: (metastable): obtained by recrystallization of propylene-glycol ($t_f$ of between 142° C. and 144° C).

These crystallized forms are distinguished by virtue of their physical-chemical properties as regards:
the melting point
heat of melting
their solubility
their spectral properties (in particular, infrared, X-ray powder diffraction).

As regards the products currently on the market, the polymorphic forms I and II coexist in different proportions. Polymorphic forms II and III could be converted into form I by boiling in water.

The presence of crystallization inhibitors can slow down this transformation.

Furthermore, the vitreous form of terphenadine could be easily obtained by rapid cooling of the melted medicine.

The crystals obtained from the currently-marketed substance are automorphic, since they have circular, laminated crystals, while polymorphic form III exists as a thin-flaked powder.

The chemical literature describes two distinct polymorphic forms of solid terphenadine having melting points of 146° C. and approximately 149°–151° C., respectively, the latter being the form which proves desirable from a commercial perspective. The procedures used to obtain both of these forms in the desired quantities have already been formulated.

In particular, European Patent Application No. EPA-0339118 describes a process for preparation of the polymorphic variety of terphenadine having a high melting point, according to which terphenadine is dissolved in a $C_1$–$C_6$ alkanol mixable in water. The solution thus obtained is heated to around its reflux temperature, and a sufficient quantity of water is slowly added while stirring in order to crystallize the terphenadine. The crystallized product is then cooled and collected.

In addition, European Patent Application No, EPA -0396100 describes a process for preparation of the polymorphic variety of terphenadine having a high melting point, in which terphenadine is dissolved in acetone, the solution is heated to the distillation point so as to remove a portion of the acetone, and the remaining mixture is gradually diluted with water, while stirring.

After crystallization of the terphenadine, the solution is cooled for several hours, and the crystallized product is collected by filtration.

However, measurement of the melting point is not a sufficiently accurate operation to verify the purity of a polymorphic form. A careful study of polymorphism utilizing differential scanning calorimetry or X-ray powder diffraction leads to the conclusion that terphenadine has three polymorphic forms having melting points of 149°–152° C., 146°–148° C., and 142°–144° C., respectively, the first being the most stable, and thus the most desirable. (see A.A. Badwan: *Analytical Profiles of Drug Substances*, 19, p. 627 (1990).

Applicants have discovered that prior art could yield products of optimal quality only with difficulty. They have developed a new purification process applicable to the high-melting-point form of terphenadine, which is the purpose of the present invention.

Another purpose of the invention is the polymorphic form of pure terphenadine having a high melting point, obtained using this procedure.

Terphenadine is readily soluble in dimethylformamide, but nearly insoluble in water.

It has been discovered that crystallization utilizing mixtures of these two solvents constantly furnished products whose X-ray diffraction spectrum proved to be exempt from contamination from polymorphic forms other than that possessing a high melting point.

Purification is carried out by mixing together water and pre-prepared solution of terphenadine in dimethylformamide. Pure terphenadine precipitates out and is collected by filtration, centrifugation, or any other conventional procedure. The mixing order is not a critical factor, but it is preferable to add the organic solution slowly to the water, while stirring.

The quantities of dimethylformamide and water used are not a critical factor and should be as small as possible for purposes of productivity. Typically, use is made of from 1 to 5 parts dimethylformamide and of from 1 to 10 parts water to one part raw terphenadine.

The ranges of variation of the various parameters were specified as the preparation process was being perfected:

It was found that a preferred range for the weight/volume ratio of terphenadine/dimethylformamide in the dissolution step was between 100 and 1000 g/l. Similarly, the terphenadine/water weight/volume ratio in the dilution step was between 50 and 2000 g/l. Moreover, the dimethylformamide/water volume/volume ratio was between 0.1 and 2.

During the step involving dissolution of terphenadine in dimethylformamide, the bath temperature should be kept at between 0° C. and 100° C.

During step involving dilution of the previously-prepared terphenadine solution in water, the temperature should be kept at between +10° C. and +90° C., and, more particularly, between 20° C. and 30° C.

EXAMPLE 500 g of raw terphenadine were dissolved in 500 ml dimethylformamide, while keeping the temperature at around 35° C. Next, the solution thus produced was poured over two hours in 2500 ml water while stirring and at between 20° C. and 25° C.

After stirring for two hours at 20° C., the crystals were filtered and washed with 500 ml water. They were put back in suspension in 3500 ml water and filtered a second time and washed with 1000 ml water.

After drying at 70°–90° C. for 24 hours, 496 g of pure terphenadine were obtained, $T_f$=150.4° C. (99.2% yield).

We claim:

1. Process for preparation of pure terphenadine in a polymorphic form having a high melting point, wherein said process consists in crystallizing the terphenadine using a mixture of water and of a solution of terphenadine in dimethylformamide, in accordance with the following steps:
   a) dissolution of the polymorphic mixture of raw terphenadine in dimethylformamide;
   b) dilution of the obtained solution, while stirring;
   c) purification by precipitation of the crystals of the polymorphic form having a high melting point; and
   d) extraction of the crystals and drying.

2. Process for preparation of pure terphenadine in a polymorphic form having a high melting point according to claim 1, wherein the terphenadine/dimethylformamide weight/volume ratio in step a) is between 100 and 1000 g/l.

3. Process for preparation of pure terphenadine in a polymorphic form having a high melting point according to claim 1, wherein the terphenadine/water weight-volume ratio in step b) is between 50 and 2000 g/l.

4. Process for preparation of pure terphenadine in a polymorphic form having a high melting point according to claim 1, wherein the dimethylformamide/water volume/volume ratio is between 0.1 and 2.

5. Process for preparation of pure terphenadine in a polymorphic form having a high melting point according to claim 1, wherein the step involving dissolution of terphenadine in dimethylformamide is carried out at between 0° C. and 100° C.

6. Process for preparation of pure terphenadine in a polymorphic form having a high melting point according to claim 1, wherein the step involving dilution of the terphenadine/dimethylformamide solution in water occurs at between 10° C. and 90° C.

7. Process for preparation of pure terphenadine in a polymorphic form having a high melting point according to claim 1, wherein the step involving dilution of the terphenadine/dimethylformamide mixture in water preferably occurs at between 20° C. and 30° C.

* * * * *